United States Patent [19]

Aarts et al.

[11] Patent Number: 5,512,204
[45] Date of Patent: Apr. 30, 1996

[54] IMINO-AZACYCLOPENTANEPOLYOL

[75] Inventors: Veronika M. L. J. Aarts, Beek, Netherlands; Dirk A. W. Stanssens, Lanaken, Belgium; Renier H. M. Kierkels, Beegden, Netherlands

[73] Assignee: DSM N.V., Heerlen, Netherlands

[21] Appl. No.: 313,023

[22] PCT Filed: Mar. 25, 1993

[86] PCT No.: PCT/NL93/00070

§ 371 Date: Jan. 9, 1995

§ 102(e) Date: Jan. 9, 1995

[87] PCT Pub. No.: WO93/20050

PCT Pub. Date: Oct. 14, 1993

[30] Foreign Application Priority Data

Mar. 27, 1992 [NL] Netherlands ............... 9200569

[51] Int. Cl.⁶ .................................... C07D 207/04
[52] U.S. Cl. ................ 252/182.13; 252/182.23; 252/182.24; 252/182.25; 252/350; 521/166; 528/73; 548/558
[58] Field of Search ............ 548/558; 252/182.13, 252/182.23, 182.24, 182.25, 350; 521/166; 528/73

[56] References Cited

U.S. PATENT DOCUMENTS

| | | | |
|---|---|---|---|
| 2,569,428 | 7/1950 | Rowland | 260/307 |
| 3,309,380 | 3/1967 | Greene | 260/326.5 |
| 4,704,411 | 11/1987 | Gansow et al. | 521/166 |
| 4,826,884 | 5/1989 | Grace et al. | 521/128 |

FOREIGN PATENT DOCUMENTS

| | | |
|---|---|---|
| 0208512 | 1/1987 | European Pat. Off. . |
| 0301297 | 2/1989 | European Pat. Off. . |

OTHER PUBLICATIONS

Chemical Abstracts, 74:140613e (1971), Amino . . . derivatives. Armand et al. p. 498.
Chemical Abstracts, 66:8018h (1967), Reactivity . . . dioxime. Buscarous et al., p. 773.
Chemical Abstracts, 67: 43591u (1967), 1,2-Cyclobutane-dicarboximidines and –dicarboximinoimides. Greene, p. 4088.
CA 77: 96640x Specific reaction of succinimidodioximes. Buscarons et al., p. 604, 1972.
CA 120: 77271t Process for . . . bis(2-oxazolines). Weerts et al., p. 879, 1994.
CA 120: 246619v N-substituted . . . reactions. Kierkels et al., p. 55, 1994.

Primary Examiner—Joseph K. McKane
Attorney, Agent, or Firm—Cushman Darby & Cushman

[57] ABSTRACT

The invention relates to novel bis-iminoazacyclo pentane polyols according to the formula given below, wherein $R^1$=H, alkyl or $R^4$, whereby $R^4$ is OH, hydroxyalkyl, hydroxyaryl or hydroxyaralkyl and $R^2$ and $R^3$ are independently of one another, OH, hydroxyalkyl, hydroxyaryl or hydroxyaralkyl which are obtainable by reaction of succinonitrile with a hydroxyalkylamine, to polyols obtained on the basis of such compounds, in which a polyether, a polyester or a vinylpolymer or combinations thereof are also incorporated, and to polymers in which said polyols are incorporated. Polyurethane foam in which 1-(hydroxyethyl)-2,5-bis-(2-hydroxyethylimino)-azacyclopentane is incorporated shows a higher mechanical strength and reduced inflammability, whilst the formulation has an increased reactivity.

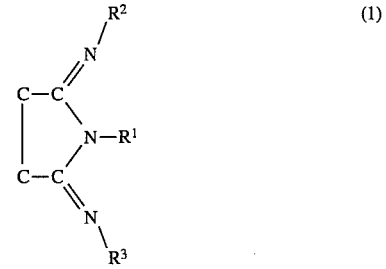

(1)

24 Claims, No Drawings

IMINO-AZACYCLOPENTANEPOLYOL

This application is a 371 of PCT/NL 93/00070 filed Mar. 26, 1993.

The invention relates to imino-azacyclopentanepolyols. Polyols of this type are novel. Polyols based on azacyclic compounds are known and are used, inter alia, as crosslinking agents or chain extenders in polymers to be produced by means of a polycondensation reaction, such as polyurethane, RIM nylon and thermosetting resins. In this context, the nitrogen-containing polyols offer the advantage of flame retardancy.

The imino-azacyclopentanepolyol according to the invention has the general formula

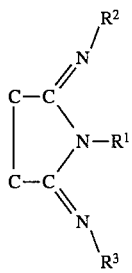

(1)

wherein $R^1$=H, alkyl or $R^4$, whereby $R^4$ is OH, hydroxyalkyl, hydroxyaryl or hydroxyaralkyl and $R^2$ and $R^3$ are independently of one another, OH, hydroxyalkyl, hydroxyaryl or hydroxyaralkyl.

Mixtures of imino-azacyclopentanepolyols according to the above formula also fall under the invention. For use as a crosslinking agent, $R^1$ is preferably $R^4$.

In another preferred embodiment of the invention, $R^1$ is H, $C_1$–$C_6$ alkyl or phenyl.

Preferably, $R^2$, $R^3$ and/or $R^4$ are chosen such that they have a hydrocarbon chain with a number of carbon atoms in the chain of between 1 and 12 and more preferably between 2 and 6. Long chains can increase the inflammability.

Preferred hydroxyalkyl groups are hydroxyalkyl groups derived from linear alkanes, because steric hindrance can easily occur in the case of branched hydrocarbons and the formation of a triol consequently becomes difficult. Specifically, the α atom, and in particular the α and β atoms, with respect to the nitrogen atom are unsubstituted.

Examples of suitable hydroxyalkyl chains are 2-hydroxyethyl, 2-hydroxypropyl, 3-hydroxypropyl, 2-hydroxy-n-butyl, 3-hydroxy-n-butyl, 4-hydroxy-n-butyl, 3-hydroxy-n-pentyl, 5-hydroxy-n-pentyl, 6-hydroxy-n-hexyl, 6-hydroxy-2-ethyl-hexyl and ω-hydroxy-dodecyl. 2-Hydroxyethyl, 3-hydroxy-propyl or 4-hydroxy-n-butyl is preferably used. Examples of hydroxyaryl and hydroxyaralkyl chains are p-hydroxy-phenyl, p-hydroxy-benzyl, p-hydroxyethylbenzyl, p-hydroxy-methylbenzyl, 5-hydroxy-3-phenylpentyl and 3-hydroxy-3-phenyl-hexyl.

Polyol derivatives (i.e. hydroxy functional oligomers or polymers) obtained with the polyols according to Formula (1) as a starting product also constitute part of the invention. Such a polyol comprises a polyether, a polyester or a vinyl polymer or combinations thereof.

Polyol derivatives of this type can be obtained using methods known per se. For example, the polyetherpolyols can be obtained by catalytic polycondensation of an alkylene oxide or a mixture of alkylene oxides in the presence of the polyol according to Formula (1).

Polyester-polyols can be prepared, for example, by reaction of the polyol according to Formula (1) with lactones, a polycarboxylic acid or the corresponding anhydride, acid chloride or ester. The polyesters can be saturated or (ethylenically) unsaturated.

One method of preparation for vinylpolymer-containing polyols is, for example, the in situ free radical polymerisation of an ethylenically unsaturated monomer or a mixture of monomers in the polyol according to Formula (1). Suitable monomers are, for example, vinyl-aromatic monomers, such as, for example, styrene, and acrylic monomers, such as, for example, acrylonitrile, methyl methacrylate, butyl acrylate and acrylic acid.

An extensive list of suitable polyethers, polyesters and vinyl polymers is to be found, inter alia, in U.S. Pat. No. 4,826,884 and the references cited therein.

Polymers in which the polyols according to Formula (1) or the polyols obtained from the polyols according to Formula (1) are incorporated and in which a polyether, a polyester or a vinyl polymer or combinations thereof are also incorporated constitute a further part of the invention.

Polymers of this type are preferably polymers which are obtained by means of a polycondensation reaction and comprise, inter alia, the thermoplastic polyesters, polyamides, in particular polyamides which can be obtained by means of anionic polymerisation of lactams, for example RIM nylons, and thermosetting resins, for example melamine formaldehyde, phenolic resins, thermosetting polyesters, and polyurethanes. Preferably, polymers of this type contain 0.01 to 20 % by weight of the polyols according to the invention, and even more preferentially 0.1 to 15% by weight.

The polymer compositions according to the invention can, if desired, also contain the customary additives, for example dyes, pigments, stabilisers, fillers, flame retardants, etc. and can be used for foams, fibres, laminates, coatings, glues as well as mouldings.

Use in foams, in particular polyurethane foam, and in a thermosetting resin composition offers particular advantages because the compound according to the invention also shows a catalytic effect on the curing reaction.

The polyol according to Formula (1) can be obtained by reaction of succinonitrile with hydroxylamine, a hydroxyalkylamine, a hydroxyarylamine or hydroxyaralkylamine, which is represented by the formula R—$NH_2$, in which R has the meaning of $R^2$, $R^3$ and/or $R^4$ (see above) and is referred to below by the abbreviation 'hydroxyamine'. If desired, mixtures of these hydroxyamines can also be used.

To this end, a melt of succinonitrile is added to the dried hydroxyamine at elevated temperature, for example about 120° C., and the reaction mixture is then allowed to react for some time (1–20 hours). After separating off any hydroxyamine still present, for example by distillation under reduced pressure, a mixture of the diol and the triol is obtained, the composition of which is highly dependent on the succinonitrile:hydroxyamine ratio chosen and the reaction time. An excess of hydroxyamine, for example in a ratio to succinonitrile of 3.4:1, yields virtually only a triol after 7 hours, whereas in the case of a ratio of 2.4:1 mainly diol is formed after 1 hour. In the latter case, $R^4$ is a hydrogen atom.

Such a diol can, if desired, be modified in a manner known per se by allowing it to react with, for example, benzylamine, ethylamine, hydroxylamine or other amine-containing compounds, which as a rule contain 1–12 carbon atoms and preferably 2–6 carbon atoms. By this reaction $R^4$ changes from being a hydrogen atom into the modifier compound.

It is also possible to start the reaction with a first hydroxyamine compound and after some time to add a second compound and to continue the reaction. In this way, the first hydroxyamine added will preferentially form $R^2$ and/or $R^3$ and the hydroxyamine added as second hydroxyamine will form the residual $R^2$ and/or $R^3$ and specifically $R^4$.

As a rule it is not necessary to use the polyol according to the invention in pure form; preferably a mixture which has a purity of more than 50%, in particular more than 80%, in an organic solvent is used.

Those skilled in the art will know how to choose the optimum reaction conditions required in order to obtain the diol, the triol or a mixture thereof, depending on the starting material. In order to shorten the reaction time, those skilled in the art will also, if desired, make use of catalysts, preferably Lewis acids, for example zinc chloride or acetates, for example zinc acetate, manganese acetate, cobalt acetate or zinc acetate.

The crude reaction product can be purified by recrystallisation from, for example, chloroform, the diol preferentially remaining behind in the solvent and the triol being obtained in solid form.

Depending on the hydroxyamine chosen, those skilled in the art will be able to adapt the preparation conditions and purification. The conditions indicated above are illustrative for the case where R is 2-hydroxy-ethyl.

Too long a reaction time has the disadvantage that a bis-oxazoline can be formed as by-product. This formation is partly dependent on the deficiency or excess of hydroxyamine which may be present. For example, if the starting materials used are hydroxyethylamine and succinonitrile, 2,2'-ethylene-bis-(2-oxazoline) can be formed.

The invention is now illustrated with the aid of the following examples and comparative examples, without, however, being restricted thereto.

EXAMPLE I 78.3 g of molten succinonitrile were added, over a period of 30 minutes, at 120° C., with stirring, to 203.3 grams of ethanolamine, which had been pre-dried over a molecular sieve (3 Å). The reaction was carried out in an inert nitrogen atmosphere. After a reaction time of 7 hours at 120° C., the free ethanolamine still present was distilled off under reduced pressure, 5 mmHg, at 60° C. The crude reaction product crystallised on cooling; m.p. 80° C. The triol formed was separated off by recrystallisation from chloroform, the diol remaining behind in the mother liquor and being obtained therefrom by evaporation.

During the reaction the conversion of the reactants was followed with the aid of $^1$H NMR. It was found that after a reaction time of 30 minutes virtually all of the succinonitrile had reacted and a mixture of the diol and the triol had formed, with a selectivity of about 30% for the triol. After a further 6 hours, the selectivity for the triol had increased to 90%.

EXAMPLE II

Example I was repeated, but now using 118 g of ethanolamine (1.96 mol) and 64 g of succinonitrile (0.8 mol). After a reaction time of 1 hour at 120° C. the synthesis was stopped. After distilling off the ethanolamine, the reaction product was recrystallised from chloroform. It was possible to separate off the triol. Evaporation of the mother liquor yielded the diol.

$^1$H NMR analysis of the reaction mixture after a reaction time of 1 hour yielded 4 mol % of succinonitrile, 32 mol % of ethanolamine, 39 mol % of diol and 25 mol % of triol.

EXAMPLES III–V AND COMPARATIVE EXPERIMENT A

The 1-(hydroxyethyl)-2,5-bis-(2-hydroxyethylimino)azacyclopentane (triol HHAC) from Example I was used in the preparation of a polyurethane rigid foam.

The components used are shown in Table 1.

TABLE 1

| Overview of the materials used in PUR rigid foam | | |
|---|---|---|
| Function | Raw material | Producer |
| polyol* | Voranol RH360 ® | DOW |
| polyol | triol HHAC | |
| blowing agent | water | |
| blowing agent | freon R11 ® | |
| surfactant | DC193 ® | DOW Corning |
| isocyanate | | |
| pol. MDI (ISO) | Mondur 44V20 ® | Bayer |
| catalyst (DBTL) | dibutyltin dilaurate | Merck |
| catalyst | TEDA L 33 ® | Tosoh |

The composition of the foam formulations with the processing characteristics are shown in Table 2.

The cream time is the time which elapses after addition of the isocyanate before a visible reaction takes place.

The rise time is the time at which the foam has reached its maximum height.

The mechanical properties and the inflammability were also determined for the product obtained in Example V, in comparison with Experiment A. The results are given in Table 3. The density of the foam was determined in accordance with ISO 845. The compressive strength (a) at 10% compression was determined in accordance with ASTM D 1621.

The LOI (limiting oxygen index) was determined in accordance with ISO 4589.

TABLE 2

| Composition of PUR rigid foam formulation and processing and physical characteristics of the foam | | | | |
|---|---|---|---|---|
| Composition (parts by wt.) | A | III | IV | V |
| Voranol RH 360 ® | 100 | 85 | 85 | 77.5 |
| triol HHAC | — | 15 | 15 | 22.5 |
| H$_2$O | 1 | 1 | 1 | 1 |
| R11 | 40 | 40 | 40 | 40 |
| DC 193 ® | 2 | 2 | 2 | 2 |
| ISO (II = 105) | 105 | 119.3 | 119.3 | 126.3 |
| DBTL | 0.1 | 0.1 | — | 0.05 |
| TEDA L 33 ® | 2 | 2 | — | 1 |
| Processing characteristics | | | | |
| cream time (s) | 24 | 10 | 15 | 11 |
| rise time (s) | 132 | 20 | 120 | 55 |

TABLE 3

Composition of PUR rigid foam formulation and processing and physical characteristics of the foam

| Composition (parts by wt.) | A | V |
| --- | --- | --- |
| Mechanical properties | | |
| σ (kPa) | 119.0 ± 6.9 | 125.4 ± 4.5 |
| Modulus of elasticity (10% compression) (MPa) | 2.75 ± 0.15 | 2.87 ± 0.15 |
| Flammability characteristics | | |
| LOI (%) | 18.5 | 19.5 |

The density of all foams is 26.9±1 kg/m³. It is found that the presence of the triol has a substantially accelerating influence on the rate of reaction. The mechanical properties and the flame-extinguishing characteristics are found to be improved.

The beneficial effect on both the preparation and the characteristics of a polymer when the polyol of the invention is incorporated therein can be seen from the above experiments.

In this context it must be pointed out that a further optimisation is possible by modification of the polyol with, inter alia, polyether and/or polyester groups etc.

We claim:

1. A polyol represented by the formula

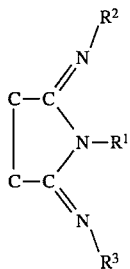

wherein $R^1$ represents H, phenyl, an alkyl group having 1–12 C-atoms, a hydroxyaryl group having 1–12 C-atoms or a hydroxyaralkyl group having 1–12 C atoms, and wherein $R^2$ and $R^3$, independently of one another, represent OH, a hydroxyalkyl group having 1–12 C-atoms, a hydroxyaryl group having 1–12 C-atoms or a hydroxyaralkyl group having 1–12 C-atoms, and wherein $R^1$ is not H when both $R^2$ and $R^3$ represent OH.

2. A polyol according to claim 1, wherein $R^1$ is OH, a hydroxyalkyl group having 1–12 C atoms, a hydroxyaryl group having 1–12 C atoms, or a hydroxyaralkyl group having 1–12 C atoms.

3. A polyol according to claim 1, wherein $R^1$ is H, $C_1$–$C_6$ alkyl, or phenyl.

4. A polyol according to claim 1, wherein $R^2$, $R^3$ and $R^4$ are individually selected from the group consisting of 2-hydroxyethyl, 2-hydroxypropyl, 3-hydroxypropyl, 2-hydroxy-n-butyl, 3-hydroxy-n-butyl, 4-hydroxy-n-butyl, 3-hydroxy-n-pentyl, 5-hydroxy-n-pentyl, 6-hydroxy-n-hexyl, 6-hydroxy-2-ethyl-hexyl and ω-hydroxydodecyl.

5. A polyol according to claim 1, wherein $R^1$ represents a hydroxyalkyl group having 2–6 carbon atoms.

6. A polyol according to claim 1, wherein $R^2$ represents a hydroxyalkyl group having 2–6 carbon atoms.

7. A polyol according to claim 1, wherein $R^3$ represents a hydroxyalkyl group having 2–6 carbon atoms.

8. A polyol according to claim 1, wherein $R^1$, $R^2$, and $R^3$ each represent a hydroxyalkyl group having 2–6 carbon atoms.

9. A polyol according to claim 1, wherein $R^1$ is 2-hydroxyethyl, 2-hydroxypropyl, or 4-hydroxy-n-butyl.

10. A polyol according to claim 1, wherein $R^2$ is 2-hydroxyethyl, 2-hydroxypropyl, or 4-hydroxy-n-butyl.

11. A polyol according to claim 1, wherein $R^3$ is 2-hydroxyethyl, 2-hydroxypropyl, or 4-hydroxy-n-butyl.

12. A polyol according to claim 1, wherein $R^1$, $R^2$, and $R^3$ each represent a hydroxyalkyl group derived from a linear alkane.

13. A curable composition for producing a polyurethane containing a catalytically and curing effective amount of a polyol represented by the formula:

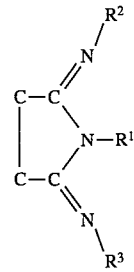

wherein $R^1$ represents H, phenyl, an alkyl group having 1–12 C-atoms, OH, a hydroxyalkyl group having 1–12 C-atoms, a hydroxyaryl group having 1–12 C-atoms or a hydroxyaralkyl group having 1–12 C atoms, $R^2$ and $R^3$, independently of one another, represents OH, a hydroxyalkyl group having 1–12 C-atoms, a hydroxyaryl group having 1–12 C-atoms or a hydroxyaralkyl group having 1–12 C-atoms, and $R^1$ is not H when both $R^2$ and $R^3$ represent OH.

14. A curable composition according to claim 13, wherein $R^1$ is OH, a hydroxyalkyl group having 1–12 C-atoms, a hydroxyaryl group having 1–12 C-atoms or a hydroxyaralkyl group having 1–12 C-atoms.

15. A curable composition according to claim 13, wherein $R^2$ represents a hydroxyalkyl group having 2–6 carbon atoms.

16. A curable composition according to claim 13, wherein $R^3$ represents a hydroxyalkyl group having 2–6 carbon atoms.

17. A curable composition according to claim 13, wherein $R^1$ represents a hydroxyalkyl group having 2–6 carbon atoms.

18. A curable composition according to claim 13, wherein $R^1$, $R^2$, and $R^3$ each represent a hydroxyalkyl group having 2–6 carbon atoms.

19. A curable composition according to claim 13, wherein $R^1$ is 2-hydroxyethyl, 2-hydroxypropyl, or 4-hydroxy-n-butyl.

20. A polyol according to claim 13, wherein $R^2$ is 2-hydroxyethyl, 2-hydroxypropyl, or 4-hydroxy-n-butyl.

21. A polyol according to claim 13, wherein $R^3$ is 2-hydroxyethyl, 2-hydroxypropyl, or 4-hydroxy-n-butyl.

22. A polyol according to claim 13 wherein $R^1$, $R^2$, and $R^3$ each represent a hydroxyalkyl group derived from a linear alkane.

23. A polyol according to claim 13, wherein $R^1$, $R^2$ and $R^3$ are individually selected from the group consisting of 2-hydroxyethyl, 2-hydroxypropyl, 3-hydroxypropyl, 2-hydroxy-n-butyl, 3-hydroxy-n-butyl, 4-hydroxy-n-butyl, 3-hydroxy-n-pentyl, 5-hydroxy-n-pentyl, 6-hydroxy-n-hexyl, 6-hydroxy-2-ethyl-hexyl and ω-hydroxy-dodecyl.

24. A polyol represented by the formula

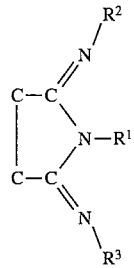

wherein $R^1$ represents H, phenyl, an alkyl group having 1–12 C-atoms, OH, a hydroxyalkyl having 1–12 C-atoms, a hydroxyaryl group having 1–12 C-atoms or a hydroxyaralkyl group having 1–12 C atoms, and $R^2$ and $R^3$, independently of one another, represent OH, a hydroxyalkyl group having 1–12 C-atoms, a hydroxyaryl group having 1–12 C-atoms or a hydroxyaralkyl group having 1–12 C-atoms, $R^1$ is not H when both $R^2$ and $R^3$ represent OH, and either (i) the alpha carbon atom of at least one of $R^1$, $R^2$, and $R^3$ is unsubstituted, said alpha atom being with respect to the nitrogen atom to which each of $R^1$, $R^2$, and $R^3$ is respectively bonded, or (ii) the alpha carbon atom and the beta carbon atom of at least one of $R^1$, $R^2$, and $R^3$ are each unsubstituted, said alpha carbon atom and said beta carbon atom being with respect to the nitrogen atom to which each of $R^1$, $R^2$, and $R^3$ is respectively bonded.

* * * * *